*(12)* United States Patent
Belcastro et al.

(10) Patent No.: US 7,032,445 B2
(45) Date of Patent: Apr. 25, 2006

(54) SYSTEM AND METHOD FOR AUTOMATICALLY MEASURING AND TRACKING A FEATURE OF MATERIAL USED DURING A MANUFACTURING PROCESS

(75) Inventors: Marc D. Belcastro, Glen Allen, VA (US); Massoud Mobrem, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 0 days.

(21) Appl. No.: 10/649,791

(22) Filed: Aug. 28, 2003

(65) Prior Publication Data

US 2005/0044948 A1    Mar. 3, 2005

(51) Int. Cl.
*G01L 5/04*    (2006.01)
(52) U.S. Cl. .......................................................... 73/159
(58) Field of Classification Search .................. 73/159, 73/38, 37.7
See application file for complete search history.

(56) References Cited

U.S. PATENT DOCUMENTS

| | | | | |
|---|---|---|---|---|
| 4,059,120 A | * | 11/1977 | Molins et al. ................ | 73/1.01 |
| 4,112,154 A | * | 9/1978 | McCarty et al. ............. | 427/401 |
| 4,121,595 A | * | 10/1978 | Heitmann et al. ........... | 131/281 |
| 4,246,775 A | * | 1/1981 | Stultz ............................. | 73/38 |
| 4,403,619 A | * | 9/1983 | Dahlgrun ..................... | 131/280 |
| 4,537,206 A | * | 8/1985 | Lorenzen et al. ............. | 73/37.7 |
| 5,412,976 A | * | 5/1995 | Vogt ................................ | 73/38 |
| 5,966,218 A | * | 10/1999 | Bokelman et al. ........... | 356/429 |
| 2003/0087740 A1 | * | 5/2003 | Brinkmann et al. ......... | 493/147 |
| 2004/0129281 A1 | * | 7/2004 | Hancock et al. ............. | 131/284 |

* cited by examiner

*Primary Examiner*—Max Noori
(74) *Attorney, Agent, or Firm*—Buchanan Ingersoll

(57) ABSTRACT

A feature of paper used in the production of a cigarette and the effect of the feature on the finished cigarette is automatically measured at specific locations along the paper, and data related to the measurement is stored in a database file. Indicia including the stored data associated with a specific location on the paper is applied at the specific location on the paper, and finished cigarettes having the indicia are collected and evaluated in order to correlate the measured value with the performance of the finished cigarette.

17 Claims, 1 Drawing Sheet

Figure 1:
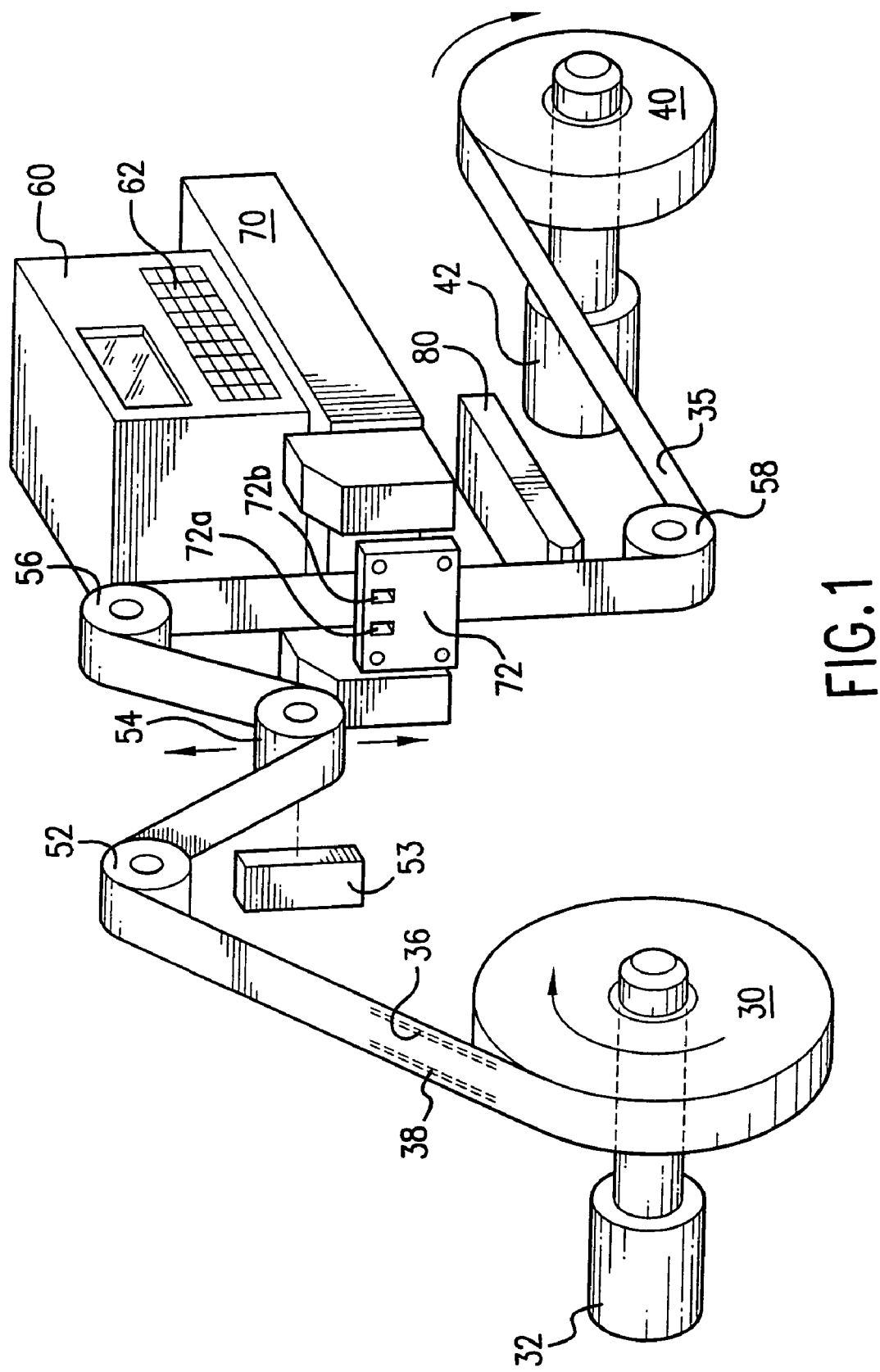

SYSTEM AND METHOD FOR AUTOMATICALLY MEASURING AND TRACKING A FEATURE OF MATERIAL USED DURING A MANUFACTURING PROCESS

FIELD OF THE INVENTION

This invention relates to the measuring and tracking of a feature of a web of material used during a manufacturing process. More particularly, the invention relates to measuring a feature of paper used in the production of a cigarette and the effect of the feature on the finished cigarette.

BACKGROUND

Webs of material such as tipping paper are used during the manufacture of cigarettes, with the tipping paper being wrapped around the filter portion of the cigarette and the tobacco rod portion of the cigarette to hold the two portions together. Rolls of the cigarette tipping paper are provided on spindles or bobbins, and undergo manufacturing operations such as laser perforation of holes in the cigarette tipping paper, with the laser perforation of the paper being performed as the paper is unwound from an unwind bobbin or spindle and rewound onto a rewind bobbin or spindle. The paper that has been processed such as by laser perforation, and then rewound on a rewind bobbin, is then supplied to another machine where the tipping paper is wrapped around cigarette filter portions and tobacco rod portions during the process of forming a finished cigarette.

SUMMARY

In accordance with an embodiment of the invention, a system and method is provided that allows for the measuring and correlation of features of materials, such as the cigarette tipping paper used in the manufacture of finished cigarettes, to the performance of individual cigarettes that are constructed with the cigarette tipping paper. A method according to an embodiment of the invention measures a feature of paper used in the production of a cigarette and allows for the determination of the effect of that feature on the finished cigarette. A feature of a web of material such as cigarette tipping paper is measured at specific locations along the paper, and data related to the measurement is stored in a database file. A sample code including the stored data associated with a specific location on the web of cigarette tipping paper can then be applied at the specific location on the paper. Finished cigarettes that have been manufactured using the marked cigarette paper can then be collected and evaluated to determine a correlation between the measured features and the performance of the finished cigarette.

A system according to embodiment of the invention for automatically inspecting a web of cigarette tipping paper at specific locations on the web of cigarette tipping paper during the manufacturing process includes an unwind spindle containing the web of cigarette tipping paper, a series of rollers over which the cigarette tipping paper is guided, a rewind spindle onto which the cigarette tipping paper is rewound, a testing device for measuring a characteristic of the cigarette tipping paper at a location on the web of cigarette tipping paper between the unwind spindle and the rewind spindle, and a printing device that is adapted to print a code including information corresponding to a measured characteristic from a particular location on the web, the printing device being positioned to print the code on the web at the particular location on the web.

BRIEF DESCRIPTION OF THE DRAWING FIGURES

FIG. 1 illustrates a system according to an embodiment of the invention.

DETAILED DESCRIPTION OF THE INVENTION

Referring to FIG. 1, a system according to an embodiment of the invention provides for automatic inspection of a web of material such as cigarette tipping paper at specific locations on the web of material during a manufacturing process. An unwind spindle 30 driven by a servo motor 32 contains a web of material 35 such as the cigarette tipping paper used during the manufacture of cigarettes. The web 35 of material on the unwind spindle 30 is guided over rollers or pulleys 52, 54, 56, and 58 before being wound onto a rewind spindle 40 driven by a servo motor 42. At least one of the rollers, such as roller 54, can be provided with an arrangement that allows for selective adjustment of the position of the roller to control the tension of the web 35. The tension of the web 35 is controlled by moving roller 54 in accordance with signals received from a tension sensor 53.

A measurement device 70 and a controller 60 are also provided in the embodiment shown in FIG. 1 to allow for automatic inspection of one or more features of the web 35 as the web is fed from unwind spindle 30 to rewind spindle 40. In the embodiment shown in FIG. 1, the measurement device 70 is a commercially available permeability inspection device that can measure the permeability of the web 35 along zones of perforations 36, 38 that have been made in the web 35 during an earlier manufacturing operation performed on the web before it is rolled on the unwind spindle 30. As shown in the embodiment of FIG. 1, two zones of perforations 36, 38 along the web 35 are measured by separate channels 72a, 72b on a measuring head 72 of the permeability measuring device 70.

The controller 60 allows for storage of data related to the measurements taken by the measurement device 70 in a database file for future use. As the web of paper is moved from unwind spindle 30 onto rewind spindle 40, a particular location that has been measured by the measurement device 70 is moved further downstream to a point where it is adjacent a printer 80 having one or more print heads. The information that is stored in the database file of controller 60 and associated with measurements taken of a particular location on the web 35 can then be included in a code printed by printer 80 on the web 35 at the same or substantially the same location where the measurement was taken. The code printed by the printer 80 can be in the form of letters, numbers, spaced bars, or other identifying indicia.

Additional functions that can be performed by the system controller 60 in accordance with user inputs at a graphical user interface 62 can include control of the servo motors 32, 42, enablement of the tension roller 54 in accordance with measurements taken by a tension sensor 53, and control of the printer 80.

In a process according to an embodiment of the invention using the system embodiment shown in FIG. 1, the web of cigarette tipping paper 35 is unwound from unwind spindle 30, permeability of the web 35 is measured at specific points, and the locations where the measurements are taken are then marked using a printer 80. After marking the web 35, the web is then rewound on rewind spindle 40. During the measurement process, the data related to the measurement and the corresponding information printed at the measurement location are collected and stored in a database file for future use. Following the permeability sampling process, the perforated web of cigarette tipping paper 35 is used to manufacture cigarettes. Cigarettes produced with this measured and marked or labeled paper are then extracted from the production flow by identifying the cigarettes that have the paper with the identifying indicia or label(s) included. These cigarettes are then subjected to laboratory testing, and the data that was originally collected, such as data related to the web's permeability, can be correlated with data collected from the evaluation of the finished cigarette. As a result, the process according to an embodiment of the invention determines a relationship between the permeability that was measured for a particular portion of the paper and its effect on the finished cigarette.

One of ordinary skill in the art will recognize that the system and method of unwinding a web of material, taking a sample measurement, and rewinding the web of material can be used for other types of measurements rather than inspection of the permeability of the web of material. In one alternative embodiment of the invention the permeability measuring device 70 could be replaced with a laser micrometer system that would allow the overall width of the web of material to be measured. In a further alternative embodiment, an optical inspection system could be provided that would inspect the surface of the web of material for any type of manufacturing printing defects or other defects in the paper itself.

A method for setting up and operating the system shown in FIG. 1, according to an embodiment of the invention, includes loading a bobbin or spindle of perforated cigarette tipping paper onto the unwind spindle 30, manually threading the paper web 35 through the tension device, which includes guide rollers 52, 54, 56 and 58, threading the web of material 35 through the permeability measuring device 70, past the printer 80 and finally onto the rewind spindle 40. Once the threading process is complete, the sampling process can be performed. Using the graphical user interface 62 on the system controller 60, a user can determine a number of test parameters that include, but are not limited to, how many samples are desired, how far apart the samples are to be taken, a target permeability, a database file name, etc. From the information entered, the system controller 60 prepares the database file, determines a unique sample code that the printer 80 produces, configures the permeability tester 70, and initializes the system.

During the initialization phase, the system controller 60 prepares the servo drives 32, 42 on the unwind spindle 30 and rewind spindle 40, enables the tension device, including a tension sensor 53 and a tension roller 54, and prepares the printer 80. Once all of the initialization procedures are complete, an operator can start the process.

A sequence of steps in an automatic sampling process can be performed according to an embodiment of the invention as follows:

1) The paper web 35 is indexed a predetermined distance.

2) The paper web 35 stops, and the permeability tester 70 takes a permeability measurement from one or more zones, e.g., as represented by channels 72a, 72b in FIG. 1, simultaneously.

3) The permeability tester 70 transfers the actual measurement data to a database in the system controller 60.

4) The paper web 35 is advanced at a slow rate through the ink jet printer 80, e.g., dual head printer, with each side or zone of the perforated paper 35 receiving a unique sample code in the exact location that the permeability measurement was taken.

5) The unique sample code for each zone is stored in the database with the corresponding permeability values.

6) The web of paper 35 is advanced at full speed until the predetermined distance is reached.

7) The process is repeated for steps 2–6 until the desired number of samples are completed.

8) Once the sampling process is completed, all the database information is saved and the system is disabled.

9) During the sampling process, if an error occurs such as a paper break, or a permeability tester fault, etc., the system controller 60 will terminate the sampling process and disable the system. All valid data will be retained.

Cigarettes that are manufactured using the web of cigarette tipping paper that has been measured and marked using an automatic sampling process such as described above, can then be extracted from the production flow by identifying the cigarettes that include the marked cigarette tipping paper. Extraction of the identified cigarettes can be performed by a human or automatically using optical recognition devices etc. The cigarettes having the sample codes or indicia can then be subjected to laboratory testing, and the data originally collected and related to a characteristic of the paper such as permeability, can be compared with data collected from the evaluation of the finished cigarettes. Whether the measurement on the web of material is related to permeability, dimensions of the web of material, the presence of out of specification conditions or characteristics on the web of material etc., the system and method according to an embodiment of the invention provides a way to correlate the measurements taken of a material such as a cigarette tipping paper with performance of specific cigarettes having that measured material.

It is to be understood that the present invention may be embodied in other specific forms, and the process of use may be varied without departing from the spirit or central characteristics of the present invention. Thus, while the invention has been illustrated and described in accordance with an embodiment, it is recognized that variations and changes may be made therein without departing from the invention as set forth in the claims.

What is claimed is:

1. A method for measuring a characteristic of cigarette tipping paper used in the production of a cigarette, said method comprising:

measuring the characteristic at one or more specific locations along the cigarette tipping paper;

storing data related to the measurement in a database file; and applying a sample code including said stored data associated with a specific location on said cigarette tipping paper at said specific location on said paper.

2. The method according to claim 1, further including:

collecting and evaluating finished cigarettes having at least one of said sample codes on said cigarette tipping paper.

3. The method according to claim 1, wherein the measured characteristic is permeability of said paper.

4. The method according to claim 3, wherein said paper is partially unwound from a bobbin before measuring said permeability.

5. The method according to claim 4, wherein said sample code is printed on said paper in the vicinity of said specific location.

6. The method according to claim 5 wherein said paper is rewound on a bobbin after printing said sample code on said paper.

7. A method for measuring a value of permeability of tipping paper used in the production of a cigarette, comprising:
   unwinding tipping paper from a bobbin of said tipping paper;
   obtaining measurements of permeability at one or more specific locations along said tipping paper;
   storing data related to said measurements in a database file;
   applying a sample code including said stored data associated with a specific location on said tipping paper at each of said one or more specific locations along said paper;
   rewinding said paper to form a bobbin of tipping paper having said one or more locations with an applied sample code; and
   using said tipping paper to produce cigarettes.

8. The method according to claim 7, further including:
   retrieving and evaluating individual cigarettes having said tipping paper with an applied sample code in correlation to said stored data associated with the specific locations on said individual cigarettes.

9. A method for automatically inspecting a web of material at specific locations on said web of material, comprising:
   unwinding said web of material from a first spindle of said material, and rewinding said web of material on a second spindle of said material,
   measuring a characteristic of said web of material at a location on said web between said first spindle and said second spindle, and
   printing a sample code selected from the group consisting of letters, numbers, spaced bars, and other identifying indicia and having information corresponding to said measured characteristic at the location where said measurement took place.

10. The method according to claim 9, further including:
    determining test parameters before said measuring of a characteristic of said web of material;
    preparing a database file including information corresponding to said test parameters; and
    incorporating said information corresponding to said test parameters on said sample code in addition to said information corresponding to said measured characteristic.

11. The method according to claim 9,
    wherein said web of material is initially unwound from said first spindle and rewound on said second spindle by a predetermined amount until said location on said web is adjacent a device for measuring said characteristic,
    stopping said initial unwinding and rewinding process and measuring said characteristic at said location while the web is stationary, and
    advancing said web of material to a position where said location on said web is printed with said sample code.

12. The method according to claim 9, wherein said advancing of said web is performed at a slower rate of speed than said initial unwinding and rewinding.

13. A system for automatically inspecting a web of material at specific locations on said web of material during a manufacturing process, comprising:
    an unwind spindle containing said web of material,
    a series of rollers over which said web of material is guided,
    a rewind spindle onto which said web of material is rewound,
    a testing device for measuring a characteristic of said web of material at a location on said web of material between said unwind spindle and said rewind spindle, and
    a printing device that is adapted to print a sample code selected from the group consisting of letters, numbers, spaced bars, and other identifying indicia and including information corresponding to a measured characteristic of a location on said web, said printing device being positioned to print said sample code on said web at said location on said web.

14. The system according to claim 13, wherein said testing device measures permeability of said web of material.

15. The system according to claim 13, wherein said testing device measures a dimension of said web of material.

16. The system according to claim 13, wherein said testing device visually inspects said web of material for out of specification conditions.

17. A system for automatically inspecting a web of cigarette tipping paper used in the production of cigarettes at specific locations on said web of cigarette tipping paper during a manufacturing process, comprising:
    means for measuring a feature of said web of cigarette tipping paper at specific locations on said web of cigarette tipping paper;
    means for storing data related to said measured feature in a database file;
    means for applying indicia including said stored data associated with a specific location on said web of cigarette tipping paper at said specific location on said web; and
    means for collecting and evaluating a finished cigarette having said indicia on said web.

* * * * *